(12) United States Patent
Tarallo

(10) Patent No.: US 8,592,480 B2
(45) Date of Patent: *Nov. 26, 2013

(54) LIQUID COMPOSITIONS OF CALCIUM ACETATE

(75) Inventor: Stephen C. Tarallo, Brockton, MA (US)

(73) Assignee: Lyne Laboratories, Inc., Brockton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/162,938

(22) Filed: Jun. 17, 2011

(65) Prior Publication Data

US 2011/0251282 A1  Oct. 13, 2011

Related U.S. Application Data

(62) Division of application No. 11/878,169, filed on Jul. 20, 2007.

(60) Provisional application No. 60/832,093, filed on Jul. 21, 2006.

(51) Int. Cl.
*A61K 31/19*  (2006.01)
*A61K 47/10*  (2006.01)

(52) U.S. Cl.
USPC ............ 514/557; 424/400; 424/439; 562/512

(58) Field of Classification Search
None
See application file for complete search history.

(56) References Cited

U.S. PATENT DOCUMENTS

| 4,093,710 | A | 6/1978 | Sass et al. |
|---|---|---|---|
| 4,870,105 | A | 9/1989 | Fordtran |
| 5,068,249 | A | 11/1991 | Long |
| 5,095,035 | A | 3/1992 | Eby |
| 5,763,449 | A | 6/1998 | Anaebonam et al. |
| 5,833,954 | A | 11/1998 | Chow et al. |
| 5,858,333 | A | 1/1999 | Winston et al. |
| 5,962,461 | A | 10/1999 | Anaebonam et al. |
| 5,976,507 | A | 11/1999 | Wong et al. |
| 6,559,187 | B2 | 5/2003 | Chandran et al. |
| 6,576,665 | B2 | 6/2003 | Dennett, Jr. et al. |
| 6,875,445 | B2 | 4/2005 | Dennett, Jr. et al. |
| 6,887,897 | B2 | 5/2005 | Walsdorf, Sr. et al. |
| 2002/0173544 | A1 | 11/2002 | Dennett et al. |
| 2003/0026872 | A1 | 2/2003 | Dake et al. |
| 2006/0228424 | A1 | 10/2006 | Nelson |

FOREIGN PATENT DOCUMENTS

| CN | 1067250 | | 12/1992 |
|---|---|---|---|
| CN | 1162489 | A | 10/1997 |
| CN | 1209322 | A | 3/1999 |
| CN | 1242963 | A | 2/2000 |
| CN | 1252278 | A | 5/2000 |
| CN | 1291456 | A | 4/2001 |
| DE | 195 28 524 | A1 | 2/1997 |
| EP | 1046410 | | 10/2000 |
| EP | 1 270 001 | A1 | 1/2003 |
| JP | 61-036222 | | 2/1986 |
| JP | 2001-204440 | | 7/2001 |
| JP | 2002-363105 | | 12/2002 |
| WO | WO-02/096393 | A1 | 12/2002 |
| WO | WO 03/047502 | * | 6/2003 |
| WO | WO 2004/045588 | A1 | 6/2004 |
| WO | WO 2004/047663 | A2 | 6/2004 |
| WO | WO-2005/117829 | A2 | 12/2005 |
| WO | WO-2006/016170 | A2 | 2/2006 |

OTHER PUBLICATIONS

Schaefer et al., Nephrology, Dialysis, Transplantation, vol. 6, pp. 170-175 (1991).*
Supplementary European Search Report issued on Jul. 17, 2009 for application No. EP 07 83 6163.
Office Action issued on Sep. 26, 2008 by the Examiner in U.S. Appl. No. 11/878,169 (US 2008/0021104).
Office Action issued on Jan. 15, 2009 by the Examiner in U.S. Appl. No. 11/878,169 (US 2008/0021104).
Office Action issued on Jul. 1, 2009 by the Examiner in U.S. Appl. No. 11/878,169 (US 2008/0021104).
Office Action issued on Feb. 5, 2010 by the Examiner in U.S. Appl. No. 11/878,169 (US 2008/0021104).
Examiner's Answer issued on Feb. 1, 2011 in U.S. Appl. No. 11/878,169 (US 2008/0021104).
European Search Report issued on Jul. 11, 2012 in application No. EP 11192965.
Mai et al., "Calcium acetate, an effective phosphorus binder in patients with renal failure," Kidney International, vol. 36, pp. 690-695, 1989.

* cited by examiner

*Primary Examiner* — Daniel Sullivan
*Assistant Examiner* — Barbara Frazier
(74) *Attorney, Agent, or Firm* — Foley & Lardner LLP

(57) ABSTRACT

The invention relates to an aqueous liquid composition of calcium acetate, sweetener, and taste masking agent. Also provided is a method for binding phosphorus within the gastrointestinal tract of an individual by administering to the individual an aqueous solution of at least calcium acetate.

39 Claims, No Drawings

LIQUID COMPOSITIONS OF CALCIUM ACETATE

This application is a divisional of U.S. application Ser. No. 11/878,169, filed Jul. 20, 2007, which claims priority under 35 U.S.C. § 119(e) to U.S. application Ser. No. 60/832,093, filed Jul. 21, 2006, both of which are hereby incorporated by reference in their entirety.

BACKGROUND OF THE INVENTION

A major focus of research and development efforts in the pharmaceutical industry is on the formulation of acceptable oral pharmaceutical compositions. More particularly, these efforts are concentrated on making oral pharmaceuticals that are palatable to the consumer. Chief among the concerns of pharmaceutical manufacturers in this area is the development of drugs that are as palatable as they are efficacious. The importance of these research efforts is greatest where the pharmaceuticals at issue are intended to ameliorate a patient's medical condition or alleviate their symptoms in cases of terminal illness. Renal diseases, such as chronic renal failure, are examples of such illnesses.

In cases of chronic renal failure, hyperphosphatemia, or excess phosphorus retention, plays a major role in the development of secondary hyperparathyroidism and osteodystrophy. Antacids or prescription medications are commonly used to manage or prevent hyperphosphatemia by binding dietary phosphorus and, thus, preventing its absorption into the gastrointestinal tract.

Phosphorous binders bind phosphorus in the form of a phosphorous ion within the stomach and intestines. This process is thought to result from a chemical reaction between dietary phosphorus and the cation present in the binder compound. The reaction causes the formation of insoluble and hence unabsorbable phosphate compounds. The cation in some phosphorous binders is aluminum or calcium. Despite their capacity for binding phosphorus, large quantities of antacids must be ingested over a long period of time for them to be effective. Therefore, dosage size and palatability are particularly important for patients with chronic renal disease.

Prescription medications typically effective in managing or preventing hyperphosphatemia include calcium acetate. Calcium acetate treatment is one of the most effective methods for management of chronic renal disease. When administered orally, calcium acetate is more effective than any other calcium-containing binder in binding phosphorus. Used alone or in combination with other materials, calcium acetate binds phosphorus in the gastrointestinal tract and reduces the percentage of consumed phosphorus (i.e., of a given "dose" of phosphorus) which is absorbed into the bloodstream. This compound is most effective in reducing phosphorous absorption when it is administered close in time to food consumption. Despite these benefits, calcium acetate treatments heretofore known in the art have not been without their drawbacks.

Calcium acetate is a solid, and to date, it is formulated in various solid dosage forms, such as pills and tablets. See, e.g., U.S. Pat. Nos. 6,875,445, 4,870,105, and 6,576,665. However, dosage forms of calcium acetate present a two-fold clinical dilemma, particularly for dialysis patients, who are a significant patient population that is treated with calcium acetate. On one hand, dialysis patients who may suffer from renal diseases such as end stage renal disease, find such solid dosage forms difficult to swallow due to their bulk size. The difficulty is exacerbated because such patients need to consume large dosages of calcium acetate, and consequently they must swallow many pills. Additionally, as mentioned above, such patients need to consume the pills prior to a meal. A third and equally undesirable characteristic of calcium acetate is that it has a repugnant bitter taste that is very unpleasant to the palate and is difficult to mask. Because solid dosage forms of calcium acetate must be able to disintegrate in the intestine, oral consumption of calcium acetate pills formulated to achieve this objective often leave particles of calcium acetate in patients' mouths, which particles leave the characteristic bad taste.

On the other hand, calcium acetate is water soluble, and liquid formulations of calcium acetate might be thought to alleviate the above-mentioned shortcomings of solid dosage forms of the drug. However, solutions of calcium acetate are many times more potently repugnant to the palate than are solid dosage forms. Additionally, it is very difficult to mask the taste of solubilized calcium acetate. Moreover, dialysis patients are restricted to limited fluid intake, and liquid dosage forms therefore could further complicate the patients' treatment regimens.

Consequently, despite the clear benefits of calcium acetate-based treatments, patients will typically fail to take the proper doses of their medicine, or they will turn to antacids as an alternative to these difficult-to-swallow unpalatable medications. The inventors are unaware of any liquid formulation of calcium acetate that could overcome the shortcomings of solid dosage forms while simultaneously addressing the above-mentioned hazards of liquid formulations. These considerations thus evidence a need in the art for liquid formulations of calcium acetate that mask the unpleasant taste, and yet are so limited in volume as to be efficacious in treating renal disease patients who are undergoing dialysis treatment.

SUMMARY OF THE INVENTION

The present invention satisfies this need and others by providing, in one embodiment, a liquid pharmaceutical composition comprising an aqueous solution of at least calcium acetate, at least one polyol, at least one sweetener, and at least one taste masking agent. In other embodiments, the liquid composition comprises about 7%, 8%, 9%, 10%, 11%, 12%, 13%, 14%, 15%, 16%, 17%, 18%, 19%, 20% or 21% calcium acetate (w/v). In other embodiments, the liquid composition comprises about 13-15%, 12-16%, or 11-17% calcium acetate (w/v); and in other embodiments the liquid composition comprises about 14% or 14.3% calcium acetate (w/v). In yet other embodiments, the liquid composition comprises about 2%, 3%, 4%, 5%, or 6% calcium acetate (w/v).

In one embodiment, five milliliters (mL) of the inventive composition provides about 710 milligrams of hydrous calcium acetate; in another embodiment, five milliliters of the inventive composition provides about 667 milligrams of anhydrous calcium acetate. In other embodiments, the inventive composition provides about 5-200 milliequivalents of calcium per five milliliters of composition. In other embodiments the inventive composition provides about 169 milligrams of calcium per five milliliters. In other embodiments, the inventive composition provides about 8 or about 8.45 milliequivalents of calcium per five milliliters. In other embodiments, the liquid composition comprises about 20% (w/v) to about 50% (w/v) of polyol (also known as sugar alcohol), or about 15% (w/v) to about 50% (w/v) of polyol. Exemplary polyols that can be used in the inventive compositions include sorbitol, xylitol, maltitol, glycerine, propylene glycol, erythritol and combinations thereof. In other embodiments, the liquid composition comprises about 15% (w/v) to about 40% (w/v) sorbitol or 15% (w/v) to about 25% (w/v)

sorbitol, or about 16% (w/v) to about 26% (w/v) sorbitol or about 18% (w/v) to about 24% (w/v) sorbitol and in other embodiments, the liquid composition comprises about 21% (w/v) sorbitol. In other embodiments the liquid composition comprises about 15% (w/v) to about 40% (w/v) of a combination of sorbitol and maltitol. In other embodiments, the liquid composition comprises about 15% (w/v) to 25% (w/v) of maltitol and in other embodiments, the composition comprises about 20% (w/v) maltitol. In other embodiments the liquid composition comprises about 1% (w/v) to about 25% (w/v) of glycerine, and in other embodiments the liquid composition comprises about 5% (w/v) glycerine. In other embodiments the liquid composition comprises about 1.5% to about 2.5% propylene glycol (w/v).

In other embodiments, the sweetener of the liquid composition is an artificial sweetener (also known in the art as a "high intensity sweetener"). Exemplary artificial sweeteners include sucralose, acesulfame potassium, aspartame, and the saccharins. In other embodiments, the artificial sweetener is selected from sucralose and saccharin. In other embodiments, the sucralose is present at a concentration of about 0.35% (w/v); in other embodiments, the concentration of sucralose is from about 0.1% (w/v) to about 0.8% (w/v). In other embodiments, the concentration of saccharin is about 0.05% (w/v) to about 0.25% (w/v) or 0.2% (w/v) to about 0.8% (w/v) and in other embodiments, the concentration of saccharin is about 0.15% (w/v).

A suitable taste masking agent for use in the inventive composition is monoammonium glycyrrhizinate (Magnasweet). In embodiments of the invention, monoammonium glycyrrhizinate is present in the composition at about 0.05% (w/v) to about 0.3% (w/v) and in other embodiments, monoammonium glycyrrhizinate is present in the composition at about 0.2% (w/v) to about 0.8% (w/v). In other embodiments the monoammonium glycyrrhizinate is present in the composition at about 0.25% (w/v).

The inventive composition may also contain a flavoring agent; suitable flavoring agents include berry flavor, root beer flavor, cream flavor, chocolate flavor, peppermint flavor, spearmint flavor and wintergreen flavor and combinations thereof. Suitable berry flavoring agents include black cherry, strawberry, cherry, blueberry, raspberry and the like. So-called "artificial" and "natural" flavoring agents are included. The inventive composition may also comprise menthol flavor.

The inventive composition may also contain one or more preservatives; exemplary preservatives include methylparaben, propylparaben, sorbic acid, sodium benzoate, potassium sorbate and combinations thereof.

The inventive composition may also contain povidone. In some embodiments, the composition comprises about 0.5% (w/v) to 1.0% (w/v) povidone, and in other embodiments, the composition comprises 0.75% (w/v) povidone. In other embodiments, the composition comprises less than about 5% (w/v), or less than about 4% (w/v), or less than about 3% (w/v), or less than about 2% (w/v), or less than about 1% (w/v) povidone. An exemplary povidone that can be used in the inventive compositions is Povidone 25.

In other embodiments, the above-described calcium acetate compositions do not contain one or more of the following ingredients: magnesium salt, calcium-peptide compounds (for example, so-called CPP-calcium), or polyvinylpyrrolidone (also known as "PVP" and "Povidone").

In one embodiment, the inventive aqueous composition comprises about 7-21% (w/v) calcium acetate, sorbitol, glycerine, monoammonium glycyrrhizinate, and sucralose. Such a composition may further comprise black cherry flavor and menthol flavor. Such a composition may further comprise propylene glycol, methylparaben, and propylparaben.

In one embodiment, the inventive aqueous composition comprises about 14.3% (w/v) calcium acetate, about 21% (w/v) sorbitol, about 5% (w/v) glycerine, about 0.25% (w/v) monoammonium glycyrrhizinate, and about 0.35% (w/v) sucralose. Such a composition may further comprise black cherry flavor and menthol flavor (exemplary amount for each flavoring agent is 0.2% (w/v)). Such a composition may further comprise propylene glycol (exemplary concentration is 2% (w/v)), methylparaben (exemplary concentration 0.05% (w/v)) and propylparaben (exemplary concentration 0.005% (w/v)). In other embodiments the amounts of black cherry and menthol flavor are provided q.s. as needed.

In a preferred embodiment, the inventive aqueous composition comprises about 7-21% (w/v) calcium acetate, sorbitol, glycerine, monoammonium glycyrrhizinate, and sucralose. Such a composition may further comprise black cherry flavor and menthol flavor. Such a composition may further comprise propylene glycol, povidone, and methylparaben.

In a preferred embodiment, the inventive aqueous composition comprises about 14.3% (w/v) calcium acetate, about 21% (w/v) sorbitol, about 5% (w/v) glycerine, about 0.25% (w/v) monoammonium glycyrrhizinate, and about 0.35% (w/v) sucralose. Such a composition may further comprise black cherry flavor and menthol flavor (exemplary amount for each flavoring agent is 0.2% (w/v)). Such a composition may further comprise propylene glycol (exemplary concentration is 2% (w/v)), methylparaben (exemplary concentration 0.2% (w/v)) and povidone (exemplary concentration 0.75% (w/v)). In other embodiments the amounts of black cherry and menthol flavor are provided q.s. as needed.

In a preferred embodiment, the inventive aqueous composition comprises about 7-21% (w/v) calcium acetate, maltitol, glycerine, monoammonium glycyrrhizinate, and sucralose. Such a composition may further comprise black cherry flavor and menthol flavor. Such a composition may further comprise propylene glycol, povidone, and methylparaben.

In a preferred embodiment, the inventive aqueous composition comprises about 14.3% (w/v) calcium acetate, about 20% (w/v) maltitol, about 5% (w/v) glycerine, about 0.25% (w/v) monoammonium glycyrrhizinate, and about 0.35% (w/v) sucralose. Such a composition may further comprise black cherry flavor and menthol flavor (exemplary amount for each flavoring agent is 0.2% (w/v)). Such a composition may further comprise propylene glycol (exemplary concentration is 2% (w/v)), methylparaben (exemplary concentration 0.2% (w/v)) and povidone (exemplary concentration 0.75% (w/v)). In other embodiments the amounts of black cherry and menthol flavor are provided q.s. as needed.

The invention also provides, in another embodiment, a method for binding phosphorus within the gastrointestinal tract of an individual, comprising administering to the individual an aqueous calcium acetate solution, as described above. In this regard, the present invention will be useful in treating individuals in need of dialysis and/or suffering from one or more of the following disorders: renal disease, kidney disease, end stage renal disease, and chronic kidney disease.

Administration of the calcium acetate composition of the present invention according to the method described herein is associated with enhanced patient compliance and fewer side effects than is evident in administering presently available calcium acetate medications and phosphorous binders. This improved patient compliance with a phosphate-binding agent will improve management of the disease process.

DETAILED DESCRIPTION

The present invention stems from the surprising discovery that calcium acetate can be formulated in a very low volume solution while simultaneously being effectively taste-masked. The liquid composition of calcium acetate according to the invention thus possesses a number of advantages over solid formulations of calcium acetate, and overcomes limitations that would otherwise be encountered in attempts to administer calcium acetate in liquid form.

First, the liquid composition obviates the need for patients to consume large numbers of pills by eliminating any calcium acetate pills. In this regard, patients taking other medications can swallow pills with the liquid composition of this invention.

Second, the composition of this invention can be formulated in very small volumes, and it therefore contributes only a negligible amount of fluid to dialysis patients' daily fluid intake.

Third, patients no longer have to swallow multiple calcium acetate pills together at the beginning of meals. Typically, the inventive composition can be ingested orally just before meals. Alternatively, the patients can swallow the inventive composition at intervals throughout their meals, or just before and just after meals. Not having to swallow multiple pills makes the overall treatment regimen a more pleasant experience, thereby ensuring high levels of patient compliance.

Fourth, the inventive composition is palatable, i.e., has a good taste, and the taste of the calcium acetate is masked, which contributes to high levels of patient compliance.

Fifth, the inventive composition can be formulated to have a low calorie content and/or a low glycemic index compared with liquid pharmaceutical formulations that are made using traditional sweeteners such as glucose and fructose. The inventive compositions are therefore suitable for administration to patients with diabetes. It is known in the art that sugars have a calorie content of about 4 calories per gram. As mentioned above, in the compositions of the present invention the sweetener can comprise a so-called artificial sweetener (sucralose, saccharin, etc.), which imparts no or negligible calories. The polyol component of the inventive compositions also imparts some sweetness, but it is known in the art that polyols (sugar alcohols) contribute fewer calories per gram than simple sugars and also have a lower glycemic index than simple sugars. For example, sorbitol has about 2.6 calories per gram and maltitol has about 3 calories per gram. In some embodiments, the inventive compositions of the invention have no more than about 1 calorie per milliliter and in other embodiments the inventive compositions have no more than about 0.8 calories per milliliter.

As discussed above, an advantage of the liquid composition is that calcium acetate can be formulated in very low volume solutions. As discussed above, typical calcium acetate concentrations range from about 7% (w/v) to about 21% (w/v), based on the total volume of the composition. In some embodiments, the concentration is from about 12% (w/v) to about 16% (w/v), and in other embodiments the concentration is about 14% or about 14.3% (w/v). The calcium acetate in the inventive composition is in aqueous solution. In still other embodiments, the calcium acetate concentration of the inventive composition is about 6% or 5% or 4% or 3% or 2% (w/v).

The liquid compositions typically supply an average dose of calcium acetate in about 10 mL or less. In some embodiments, the volume can range from about 4 mL to about 7 mL. Illustrative of the volume of a dose is a composition measuring about 5 mL, which delivers the equivalent of one (1) tablet of a solid calcium acetate formulation, i.e., pill. Such a 5 mL dose can supply about 710 milligrams of hydrous calcium acetate, or about 667 milligrams of anhydrous calcium acetate. Thus, for example, merely a tablespoon of the present composition (i.e., ~15 mL) would replace three (3) conventional calcium acetate pills. In other embodiments, 5 mL supplies about 1.065 grams of hydrous calcium acetate or about 1.0 gram of anhydrous calcium acetate.

The composition of the invention comprises a taste masking agent. Some taste masking agents known in the art are characterized additionally as sweeteners. Regardless of whether a particular compound is recognized for imparting sweetness, it should at least possess the property of being able to mask tastes in the mouth. An exemplary taste masking agent in this regard is monoammonium glycyrrhizinate (Magnasweet).

The inventive composition also comprises a sweetener. Various sweeteners are contemplated, including but not limited to simple sugars such as sucrose, dextrose, fructose, maltose, and the like. In other embodiments, the inventive composition is "low calorie" or "light", "sugar-free", or "calorie-free." As discussed above, the sweetener in the inventive compositions may be a so-called "artificial sweetener" (also known as "high-intensity sweetener"), such as sucralose, acesulfame potassium, saccharin, and aspartame, or any combination thereof. The use of such artificial sweeteners is desirable for adding sweetness without the addition of calories. Also as discussed above, the polyol in the inventive composition may also provide some sweetening and the lower calorie content of polyols, and lower glycemic index (compared to simple sugars) make the inventive compositions suitable for low calorie diets. Additionally, the inventive compositions that are low calorie and/or low glycemic index would be suitable for diabetic patients.

One of skill in the art will recognize that the "sugar-free" means that a product contains no amount of, or only trivial or "physiologically inconsequential" amounts of sugars. In this regard, "sugar free" means less than 0.5 g of sugars per serving. "Calorie free" means fewer than 5 calories per serving. Examples of synonyms for "free" include "without," "no" and "zero." Those products sweetened only with artificial sweeteners and/or sugar alcohols (and containing no other sugars) can be classified as "sugar-free." The term "low calorie" is understood to mean 40 calories or less per reference amount.

In one embodiment, the composition comprises the sweetener sucralose and the polyol sorbitol, and the taste masking agent monoammonium glycyrrhizinate. In another embodiment, the composition comprises the sweetener sucralose and the polyols sorbitol and maltitol, and the taste masking agent monoammonium glycyrrhizinate. In another embodiment, the composition comprises the sweetener sucralose and the polyol maltitol, and the taste masking agent monoammonium glycyrrhizinate.

As discussed above, the composition of the invention contemplates various concentrations of calcium acetate, a taste masking agent, and a sweetener to achieve a palatable composition.

In other embodiments, the taste masking agent is present in a concentration of about 0.05% (w/v) to about 0.8% (w/v) based on the total volume of the composition. Exemplary concentrations are about 0.05%, 0.1%, 0.15%, 0.2%, 0.25%, 0.3%, 0.35%, 0.4%, 0.45%, 0.5%, 0.55%, 0.6%, 0.65%, 0.7%, 0.75% and 0.8% (w/v). In other embodiments, the taste masking agent is present in a concentration of about 0.2% (w/v) to about 0.8% (w/v) based on the total volume of the composition. Exemplary concentrations are about 0.25%, 0.3%, 0.4%, 0.5%, 0.6%, 0.7% and 0.8% (w/v).

A preferred composition prescribed by the foregoing considerations, and for use in the methods described herein, comprises calcium acetate in a concentration about 14%

(w/v), maltitol in a concentration of about 20% (w/v), sucralose in a concentration of about 0.35% (w/v), and monoammonium glycyrrhizinate in a concentration of about 0.25% (w/v), based upon the total volume of the composition.

A preferred composition prescribed by the foregoing considerations, and for use in the methods described herein, comprises calcium acetate in a concentration of about 14% (w/v), sorbitol in a concentration of about 21% (w/v), sucralose in a concentration of about 0.35% (w/v), and monoammonium glycyrrhizinate in a concentration of about 0.25% (w/v), based upon the total volume of the composition.

The inventive composition may also contain a flavoring agent; suitable flavoring agents include berry flavor, root beer flavor, cream flavor, chocolate flavor, peppermint flavor, spearmint flavor and wintergreen flavor and combinations thereof. Suitable berry flavoring agents include black cherry, strawberry, cherry, blueberry, raspberry and the like. So-called "artificial" and "natural" flavoring agents are included. The inventive composition may also comprise menthol flavor. The amounts of the flavoring agents used will vary depending on taste preferences and the other ingredients in the composition, but will be a very small percentage of the overall composition; for example, in Examples 1-4, the artificial black cherry flavor and menthol are each present at a concentration of 0.2% (w/v). In a typical composition of the invention, the flavoring agents will typically make up no more than 1% (w/v) of the calcium acetate composition.

Other ingredients which may be present in the liquid composition of the present invention include buffers, such as citric acid or its corresponding salts; surfactants; thickeners (such as methylcellulose, carboxymethylcellulose, polyvinylpyrrolidone, and the like); preservatives (such as methyl and propyl parabens, and the like; anti-oxidants, such as benzoate salts, and the like; chelating agents, such as EDTA and its salts and the like). The amount and type of preservative present in the liquid composition of the invention can be determined as known by those of skill in the art. For example, methylparaben can be used in a concentration of from 0.01% (w/v) to about 0.2% (w/v), or from about 0.1% (w/v) to about 0.3% (w/v) and propylparaben can be used in a concentration of from about 0.001% (w/v) to about 0.05% (w/v). Povidone can be used in a concentration of about 0.5% (w/v) to about 1.0% (w/v).

In a preferred embodiment, the concentration of methylparaben is about 0.2% (w/v) and the concentration of povidone is about 0.75% (w/v). In another embodiment, the composition of methylparaben is about 0.05% (w/v) and the concentration of propylparaben is about 0.005% (w/v); in another embodiment, the composition of methylparaben is about 0.01% (w/v) and the concentration of propylparaben is about 0.025% (w/v).

As discussed above, the inventive compositions also include liquid calcium acetate compositions that do not contain one or more of the following ingredients: magnesium salt, calcium-peptide compounds (for example, so-called CPP-calcium), or polyvinylpyrrolidone (PVP).

In various embodiments, the inventive composition can be formulated to have a final pH of about 6.0 to about 7.0. Alternatively, the pH can be about 6.0 to about 7.2. In one embodiment, the pH of the inventive composition is about 6.8.

Any of the embodiments of the liquid composition herein described are suitable for use in the inventive method for binding phosphorus within the gastrointestinal tract of an individual. The method comprises administering to the individual an aqueous solution of at least calcium acetate as described herein. The administration, in one embodiment, is via oral ingestion of the composition. As discussed, the use of calcium acetate to treat hyperphosphatemia is well known in the art, and hence the dosages required to treat this condition can also be readily determined depending on patient condition, history and need. In this regard, as discussed above, the typical dose of calcium supplied by calcium acetate is on the order of about 10 to about 200 milliequivalents of calcium per dose. A typical dosage regimen of the inventive composition is about one tablespoon (about 15 mL) three times per day, which can be varied depending on the needs of the patient.

Furthermore, those of skill in the art will understand that the dose or quantity to be taken at a given time varies on an individual basis and can be adjusted as needed, for example by monitoring the serum levels of phosphorus and calcium. In this regard, the inventive compositions are preferably administered close in time to food and/or beverage consumption. In one embodiment, a dose of the inventive composition is taken orally just before meal ingestion and another dose is taken orally just after meal ingestion. As discussed herein, the entire dose administered around a meal may all be taken just prior to ingestion of a meal.

In some embodiments, the individual to be treated is in need of dialysis treatment and hence may be undergoing such dialysis treatment. In various embodiments, the individual is suffering from a renal disease, such as, for example, end stage renal disease or chronic kidney disease.

The following examples are intended to illustrate the invention as is hereinabove more generally described, and therefore they should not be construed to limit the scope of the invention. Furthermore, all documents cited herein, including U.S. patents, are fully incorporated as if fully set forth herein.

EXAMPLE 1

General Procedure to Prepare Calcium Acetate Liquid Composition

Calcium acetate and a sweetener are dissolved in water. Flavoring and glycerin USP are mixed with each other to eventually obtain a homogeneous solution. A taste masking agent is added to and mixed with the calcium acetate solution. Parabens preservatives are dissolved in propylene glycol. Optionally an additional taste masking or sweetening agent is mixed with the calcium acetate solution. All solutions including any other polyols are agitated together and purified water is added q.s. to achieve a homogeneous solution.

EXAMPLE 2

Calcium Acetate Liquid Compositions

Following the general procedure of Example 1, a 1.0 L liquid calcium acetate composition was prepared using the following concentrations and proportions of components:

| Component | Amount | % w/v |
| --- | --- | --- |
| Sorbitol solution (70%) | 300 g | 30 |
| Calcium acetate USP | 143 g | 14.3 |
| Glycerine USP | 50 g | 5 |
| Propylene Glycol USP | 20 g | 2 |
| Magnasweet 110 (10% solution) | 25 g | 2.5% |
| Sucralose | 3.5 g | 0.35 |
| Methylparaben NF | 0.5 g | 0.05 |
| Propylparaben NF | 0.05 g | 0.005 |

-continued

| Component | Amount | % w/v |
|---|---|---|
| Artificial black cherry flavor | 2 g | 0.2 |
| Menthol flavor | 2 g | 0.2 |
| Purified water USP q.s. | 1000 ml | |

Note that because a 70% solution of sorbitol was used, the % of sorbitol compound in the final composition is 21%. This composition contains about 0.5 calories per milliliter. Multiple people tasted this composition at typical dosage levels, and all people who tested this composition rated the composition as palatable and/or having "good" flavor. It was determined that this composition would be suitable for administration to patients and that those patients would be expected to comply well with their medication requirements, given the qualities of the composition (including but not limited to, palatability and low volume of liquid with high concentration of calcium). For those patients needing to limit calorie intake, this composition is suitable because of its low calorie content.

In another example, the calcium acetate liquid composition of this example is formulated using 0.1% (w/v) methylparaben and 0.025% (w/v) propylparaben. In yet another example, the flavoring agents are added q.s. to achieve a palatable taste with the minimum effective amount of flavoring agent.

EXAMPLE 3

Following the general procedure of Example 1, a 1.0 L liquid calcium acetate composition was prepared using the following concentrations and proportions of components:

| Component | Amount | % w/v |
|---|---|---|
| Sorbitol solution (70%) | 300 g | 30 |
| Calcium acetate USP | 143 g | 14.3 |
| Glycerine USP | 50 g | 5 |
| Propylene Glycol USP | 20 g | 2 |
| Magnasweet 110 (10% solution) | 25 g | 2.5 |
| Sucralose | 3.5 g | 0.35 |
| Povidone 25, USP | 7.5 g | 0.75 |
| Methylparaben NF | 2 g | 0.2 |
| Artificial black cherry flavor | 2 g | 0.2 |
| Menthol flavor | 2 g | 0.2 |
| Purified water USP q.s. | 1000 ml | |

Note that because a 70% solution of sorbitol was used, the % of sorbitol compound in the final composition is 21%. This composition contains about 0.5 calories per milliliter. Multiple people tasted this composition at typical dosage levels, and all people who tested this composition rated the composition as palatable and/or having "good" flavor. It was determined that this composition would be suitable for administration to patients and that those patients would be expected to comply well with their medication requirements, given the qualities of the composition (including but not limited to, palatability and low volume of liquid with high concentration of calcium). For those patients needing to limit calorie intake, this composition is suitable because of its low calorie content.

EXAMPLE 4

Following the general procedure described below, a 2.0 L liquid calcium acetate composition was prepared using the following concentrations and proportions of components:

| Component | Amount | % w/v |
|---|---|---|
| Maltitol (crystalline) | 400 g | 20 |
| Calcium acetate USP | 286 g | 14.3 |
| Glycerine USP | 100 g | 5 |
| Propylene Glycol USP | 40 g | 2 |
| Magnasweet 110 (10% solution) | 50 g | 2.5 |
| Sucralose | 7 g | 0.35 |
| Povidone 25 USP | 15 g | 0.75 |
| Methylparaben NF | 4 g | 0.2 |
| Artificial black cherry flavor | 4 g | 0.2 |
| Menthol flavor | 4 g | 0.2 |
| Purified water USP q.s. | 2000 ml | |

Calcium acetate was dissolved in 1 liter of water and sucralose was added to this aqueous mixture, followed by the addition of maltitol with agitation, then glycerin, then Magnasweet with agitation and then Povidone was added and mixed until dissolved. Methylparaben was dissolved in propylene glycol and added to the aqueous mixture with agitation. The flavors were then added with agitation. Additional water was added to bring the total volume to 2 liters.

This composition contains about 0.4 calories per milliliter. Multiple people tasted this composition at typical dosage levels, and all people who tested this composition rated the composition as palatable and/or having "good" flavor. It was determined that this composition would be suitable for administration to patients and that those patients would be expected to comply well with their medication requirements, given the qualities of the composition (including but not limited to, palatability and low volume of liquid with high concentration of calcium). For those patients needing to limit calorie intake, this composition is suitable because of its low calorie content.

What is claimed is:

1. A method for binding phosphorus within the gastrointestinal tract of an individual, comprising orally administering to said individual a liquid pharmaceutical composition comprising an aqueous solution comprising
    (a) 7-16% calcium acetate (w/v), based on the total volume of the composition,
    (b) a sweetener,
    (c) a polyol, and
    (d) a taste masking agent.

2. The method according to claim 1, wherein the individual is in need of dialysis and/or is suffering from one or more of the following disorders: renal disease, kidney disease, end stage renal disease, chronic kidney disease.

3. The method according to claim 1, wherein the composition comprises: calcium acetate in a concentration of about 12% (w/v) to about 16% (w/v) based on the total volume of the composition.

4. The method according to claim 1, wherein the calcium acetate is present in a concentration of about 14% (w/v).

5. The method according to claim 1, wherein the total concentration of polyol in the composition is about 15% (w/v) to about 50% (w/v) based on the total volume of the composition.

6. The method according to claim 1, wherein said polyol is selected from the group consisting of sorbitol, glycerine, propylene glycol, xylitol, maltitol, and combinations thereof.

7. The method according to claim 6, wherein said composition comprises about 15% (w/v) to about 40% (w/v) of sorbitol based on the total volume of the composition.

8. The method according to claim 6, wherein said composition comprises about 21% (w/v) sorbitol.

9. The method according to claim 6, wherein said composition comprises about 15% (w/v) to about 25% (w/v) maltitol based on the total volume of the composition.

10. The method according to claim 6, wherein said composition comprises about 20% (w/v) maltitol.

11. The method according to claim 1, wherein said composition further comprises about 1% (w/v) to about 25% (w/v) of glycerine based on the total volume of the composition.

12. The method according to claim 11, wherein said glycerine is present at a concentration of about 5% (w/v).

13. The method according to claim 1, wherein said sweetener is an artificial sweetener.

14. The method according to claim 13, wherein said artificial sweetener is selected from the group consisting of sucralose, acesulfame potassium, aspartame and saccharin.

15. The method according to claim 13, wherein said artificial sweetener is selected from the group consisting of sucralose and saccharin.

16. The method according to claim 15, wherein said sucralose is present at a concentration of about 0.35% (w/v) or said saccharin is present at a concentration of about 0.15% (w/v) based on the total volume of the composition.

17. The method according to claim 1, wherein said composition further comprises at least one flavoring agent.

18. The method according to claim 17, wherein said flavoring agent is selected from the group consisting of menthol, berry flavor, root beer flavor, cream flavor, chocolate flavor, peppermint flavor, spearmint flavor and wintergreen flavor.

19. The method according to claim 18, wherein said flavoring agent is black cherry flavor.

20. The method according to claim 19, wherein said black cherry flavor is artificial black cherry flavor.

21. The method according to claim 19, wherein said composition further comprises menthol flavor.

22. The method according to claim 1, wherein said composition further comprises at least one preservative.

23. The method according to claim 22, wherein said preservative is selected from the group consisting of methylparaben, propylparaben, sorbic acid, sodium benzoate, potassium sorbate and combinations thereof.

24. The method according to claim 23, wherein said preservative comprises methylparaben.

25. The method according to claim 1, wherein said composition comprises polyvinylpyrrolidone (PVP).

26. The method according to claim 1, wherein said polyol comprises propylene glycol.

27. The method according to claim 1, wherein said composition has pH of about 6.0 to about 7.2.

28. The method according to claim 1, wherein said taste masking agent comprises monoammonium glycyrrhizinate.

29. The method of claim 1, wherein 5 milliliters of said composition contains about 710 milligrams of hydrous calcium acetate.

30. The method of claim 1, wherein 5 milliliters of said composition contains about 667 milligrams of anhydrous calcium acetate.

31. The method of claim 1, wherein 5 milliliters of said composition contains about 169 milligrams of calcium.

32. The method of claim 1, wherein said composition is sugar-free.

33. The method of claim 1, wherein said composition is a low-calorie composition.

34. The method of claim 1, wherein said composition is calorie-free.

35. The method of claim 1, wherein said composition comprises about 8 milliequivalents of calcium.

36. The method according to claim 1, wherein the individual s suffering from hyperphosphatemia.

37. The method according to claim 1, wherein the method comprises administering about one tablespoon (15 mL) of said composition three times per day.

38. The method according to claim 1, wherein the method comprises administering said composition around the time of ingestion of a meal.

39. The method according to claim 25, wherein said composition comprises from about 0.5% to about 1.0% (w/v) polyvinylpyrrolidone (PVP), based on the total volume of the composition.

* * * * *